United States Patent [19]
Govorkov

[11] Patent Number: 5,688,049
[45] Date of Patent: Nov. 18, 1997

[54] METHOD AND APPARATUS FOR MEASURING THE THERMAL CONDUCTIVITY OF THIN FILMS

[75] Inventor: Sergei V. Govorkov, Nanuet, N.Y.

[73] Assignee: Inrad, Northvale, N.J.

[21] Appl. No.: 591,051

[22] Filed: Jan. 25, 1996

[51] Int. Cl.$^6$ .................................................. G01N 25/18
[52] U.S. Cl. ................................................................ 374/44
[58] Field of Search .................................. 374/43, 44, 45, 374/117, 120, 143

[56] References Cited

U.S. PATENT DOCUMENTS

| | | | |
|---|---|---|---|
| 4,764,023 | 8/1988 | White et al. | 374/43 |
| 5,010,250 | 4/1991 | Elsayed-Ali | 374/41 |
| 5,217,304 | 6/1993 | Ortiz | 374/44 |
| 5,335,993 | 8/1994 | Marcus et al. | 374/11 |

FOREIGN PATENT DOCUMENTS

| | | | |
|---|---|---|---|
| 58-202863 | 11/1983 | Japan | 374/44 |
| 62-134547 | 6/1987 | Japan | 374/44 |
| 920489 | 4/1982 | U.S.S.R. | 374/44 |

OTHER PUBLICATIONS

Thermal Conductivity of Coatings, Laser Method for Determining Thermal Conductivity (no date).

Lambropoulus, J.C. et al., "Thermal conductivity of dielectric thin films", J. Appl. Phys., vol. 66, No. 9, pp. 4230–4242, Nov. 1, 1989.

Henager, Jr., C.H. et al., "Thermal conductivities of thin, sputtered optical films", Applied Optics, vol. 32, No 1, pp. 91–101, Jan. 1, 1993.

Wu, Z.L. et al., "Absorption and thermal conductivity of oxide thins films . . .", Applied Optics, vol. 32, No. 28, pp. 5660–5665, Oct. 1, 1993.

Krishnan, S. et al., "The Use of Thin Film Thermocouples to Determine the Thermal Conductivity . . .", J. Adhesion, vol. 42, pp. 103–112, 1993.

Cahill, D.G. "Thermal conductivity measurement from 30 to 750 K . . .", Rev. Sci. Instrum, vol. 61, No. 2, pp. 802–808, 1990.

Griffin, Jr. A.J. et al., "Effect of thickness on the transverse thermal conductivity . . .", J. Appl. Physics, vol. 75, No. 8, pp. 3761–3764, Apr. 15, 1994.

*Primary Examiner*—G. Bradley Bennett
*Attorney, Agent, or Firm*—Stroock & Stroock & Lavan LLP

[57] ABSTRACT

A device and method for measuring the thermal conductivity of a thin film by determining the change in temperature near the surface of the film after a sample including the film is illuminated with a beam of light. This can be accomplished by modulating the beam of light at a selected modulation frequency and measuring the amplitude of the sound waves created in the gas near the surface of the sample as a result of the repetitive heating and cooling of the surface. The amplitude of the sound signal will be directly proportional to the thermal resistivity of the thin film, provided that the modulation frequency is selected within an appropriate range. In a preferred embodiment of the invention, a portion of the thin film is removed from (or not deposited on) the substrate and the entire surface of the substrate, including the portion coated with the thin film and the bare half is coated with a layer of covering material, such as graphite or metal. The amplitude of the sound signal generated by the layer of covering material on the bare substrate surface is then subtracted from the amplitude of the signal generated by the two layer side of the substrate. The remainder is essentially equal to the portion of the amplitude contributed by the thermal resistivity of the thin film itself. In this manner, even transparent thin films which do not heat appreciably upon illumination can be evaluated.

39 Claims, 3 Drawing Sheets

METHOD AND APPARATUS FOR MEASURING THE THERMAL CONDUCTIVITY OF THIN FILMS

BACKGROUND OF THE INVENTION

The invention relates generally to measuring the thermal conductivity of thin films and more particularly to a relatively simple device sensitive enough to make rapid nondestructive measurements of the thermal conductivity of thin films, having thicknesses as low as 1 µm and even substantially less.

Thin films are used extensively in various fields, such as optics, microelectronics, data storage and areas in which a coating having high thermal conductivity or high thermal resistivity are needed. Knowing the thermal conductivity of the actual film used can be especially important for determining information such as heat dissipation rates, which can be important to the construction of microelectronic devices. Determining the thermal conductivity can also provide important information about the film itself, because thermal conductivity is strongly related to the microstructure and properties of the film.

Determining the thermal conductivity of a thin film presents several problems. One is that the thermal conductivity of a thin film is generally different than the thermal conductivity of the material in bulk. For example, many different types of oxide thin films used in optical coatings have been found to have thermal conductivities that are substantially lower than of bulk samples of the same material. This difference in thermal conductivity has been attributed in part to the particularities of thin film growth.

Existing techniques for measuring the thermal conductivity of thin layers of material tend to be either limited to thick films of greater than about 10 µm, due to lack of sensitivity or are too cumbersome and time consuming to implement in an industrial environment for on-line control. Such conventional techniques can be time consuming, labor intensive, complicated and more appropriate for a laboratory setting than production facilities. Often, the thermal resistance of the interfaces between the film and heaters, heat sinks, probe tips and the like obscure the results sought.

One commercial instrument for determining the thermal conductivity of a thin film utilizes a transient technique for measuring the thermal diffusivity of materials. The surface of a sample of material is illuminated with a pulsed laser and an infrared detector measures temperature rise at the back surface of the sample as a function of time. However, this method is destructive, suffers from a relatively low sensitivity and precludes measurement of films in the 0.1–10 µm range of thickness. Furthermore, knowledge of the specific heat of the thin film is required to deduce the thermal conductivity.

Other techniques, referred to as thermal comparator methods, discussed in Lambropoulos, et al. *J. of Appl. Phys.*, 1989, 66, 4230–4242 and Henager, et al. *Appl. Optics*, 1993, 32, 91–101, the contents of which are incorporated herein by reference, describe contacting a copper tip of a probe directly to the surface of the thin film. This technique can damage some soft films. It also involves problems of reproducibility of the tip/film interface thermal resistance, which tends to limit the accuracy and sensitivity of the method. It requires careful characterization of the contact area and therefore, trained users. Sensitivities of $2\times10^{-6}$ m$^2$K/W, film thicknesses of 2000 Å and accuracies of ±73% are common. Moreover, the apparatuses involved are difficult to operate, require specially trained personnel and involve the preparation of films of varying thicknesses.

Photothermal reflectance and photothermal deformation techniques are discussed in Wu, et al., *Appl. Optics*, 1993, 32, 5660–5665, the contents of which are incorporated herein by reference. The techniques discussed can be used to obtain information regarding the thermal conductivity of a sample surface layer, but are severely limited in sensitivity. Moreover, the techniques involve complicated hardware and special training for operators.

Still another method of determining information about the thermal conductivity of thin films is based on modulated differential scanning calorimetry, as described in U.S. Pat. No. 5,335,993, the contents of which are incorporated herein by reference. However, the method described therein has insufficient sensitivity, in part, because it measures the conductivity of massive bodies brought into thermal contact with thin film wafers and does not fully eliminate interface thermal resistance.

A method of providing results that are more accurate than those discussed above can be obtained by the direct deposition of metal films or metal micro strips onto the surface of the film to be measured, such as is set forth in Krishana, et al., *J. Adhesion*, 1993, 42, 103–112, Cahill, *Rev. Sci. Instrum.*, 1990, 58, 802–808, and Griffin, et al. *J. Appl. Phys.*, 1994, 75, 3761–3764, the contents of which are incorporated herein by reference. The techniques discussed therein employ metal films deposited onto the surface of the film to be measured as heaters and temperature sensors. However, such techniques require vacuum deposition equipment, special training, considerable time and are inadequately simple, rapid or nondestructive.

Accordingly, it is desirable to provide a simple, rapid and nondestructive technique for measuring the thermal conductivity of thin films, particularly one that is sensitive enough to measure the conductivity of films as thin as 0.1 µm and smaller, is suitable for on-line control in an industrial production setting and overcomes other drawbacks of the prior art.

SUMMARY OF THE INVENTION

Generally speaking, in accordance with the invention, the thermal conductivity of a thin film is measured by determining the change in temperature of the surface of the film after a sample including the film is illuminated with a beam of light. This can be accomplished by modulating the intensity of a beam of light at a selected modulation frequency and measuring the amplitude of the sound waves created in the gas near the surface of the sample as a result of the repetitive heating and cooling of the surface. By amplifying the electrical signal the sound causes a microphone to create and filtering the noise outside of the selected frequency, this amplitude can be measured with a simple volt meter. The amplitude of the sound signal will be directly proportional to the thermal resistivity of the thin film, provided that the modulation frequency is selected within an appropriate range. By keeping all variables of the measurement process constant, except for the thin film tested, the thermal conductivity of the film can be determined by comparing the voltage output to a set of standard values.

In a preferred embodiment of the invention, a thin film of the material to be measured is deposited on the surface of a substrate. A portion of the thin film is then removed and the entire surface of the substrate, including the portion coated with the thin film and the bare half is coated with a layer of covering material, such as graphite or metal. Alternatively, the thin film of the material is only deposited on a portion of the surface of a substrate by masking or other suitable techniques. The covering material should be opaque and have high thermal conductivity. The amplitude of the sound signal generated by the layer of covering material on the bare substrate surface is then subtracted from the amplitude of the signal generated by the two layer side of the substrate. The remainder is essentially equal to the portion of the amplitude contributed by the thermal resistivity of the thin film itself. In this manner, even transparent thin films which do not heat appreciably upon illumination can be evaluated.

Accordingly, it is an object of the invention to provide a method for the rapid, nondestructive measurement of the thermal conductivity and thermal resistance of thin films.

Another object of the invention is to provide a method for measuring the thermal conductivity of thin films in a production line setting.

Still another object of the invention is to provide a simple relatively inexpensive apparatus for measuring the thermal conductivity and thermal resistivity of thin films.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description, taken in connection with the accompanying drawings, in which.

DETAILED DESCRIPTION OF THE PREFERRED EMBODIMENTS

The invention is directed to a method and apparatus for measuring the thermal resistance and therefore the thermal resistivity, conductance and conductivity of solid thin films on solid substrates by measuring the change of the temperature of the film after illuminating the film with electromagnetic radiation, such as visible light. In a preferred embodiment, the change in temperature is determined by measuring the amplitude of the acoustic signal (acoustic volume) generated in the gas (such as air) near the surface of the film. This acoustic signal results from the change in volume of air or other gas adjacent the thin film surface, as the thin film is warmed by the illumination. The sudden change in volume creates a pulse or sound wave in the gas adjacent the surface. By modulating the intensity of the illumination of the surface, a sound signal having a frequency corresponding to the frequency of the modulation is generated. By using this technique, sensitivities of $1 \times 10^{-7}$ m$^2$K/W for film thicknesses of 100 Å and accuracies of ±5% and better can be achieved.

The amplitude of the sound waves are directly proportional to the thermal resistance of the thin film under examination. If the sample is coupled to a heat sink, highly conductive thin films will cause a relatively weak sound signal, because the heat will flow to the heat sink before there is much warming of the gas adjacent the illuminated surface. In contrast, a thin film with high thermal resistance will be unable to transfer the energy absorbed to the heat sink quickly enough to prevent substantial warming. This warming will generate a strong pulse of expanded air, which can be detected by various means, including a relatively inexpensive microphone.

Determining the resistance to heat flow can be used to calculate thermal conductivity and resistivity. When the thickness of the film ($d_f$) is known, the effective thermal conductivity of the film ($k_f$) can be calculated from formula I:

$$k_f = d_f R_f \qquad (I)$$

wherein $R_f$ is the measured thermal resistance of the film. Film thickness can be measured by various methods such as optical measurements, stylus methods and others. Determining the conductivity also provides the resistivity. The effective thermal conductivity $k_f$, accounts generally for the contribution of the thermal resistance of the interface between the film and substrate, in addition to the thermal resistance of the film itself.

Figure 1:
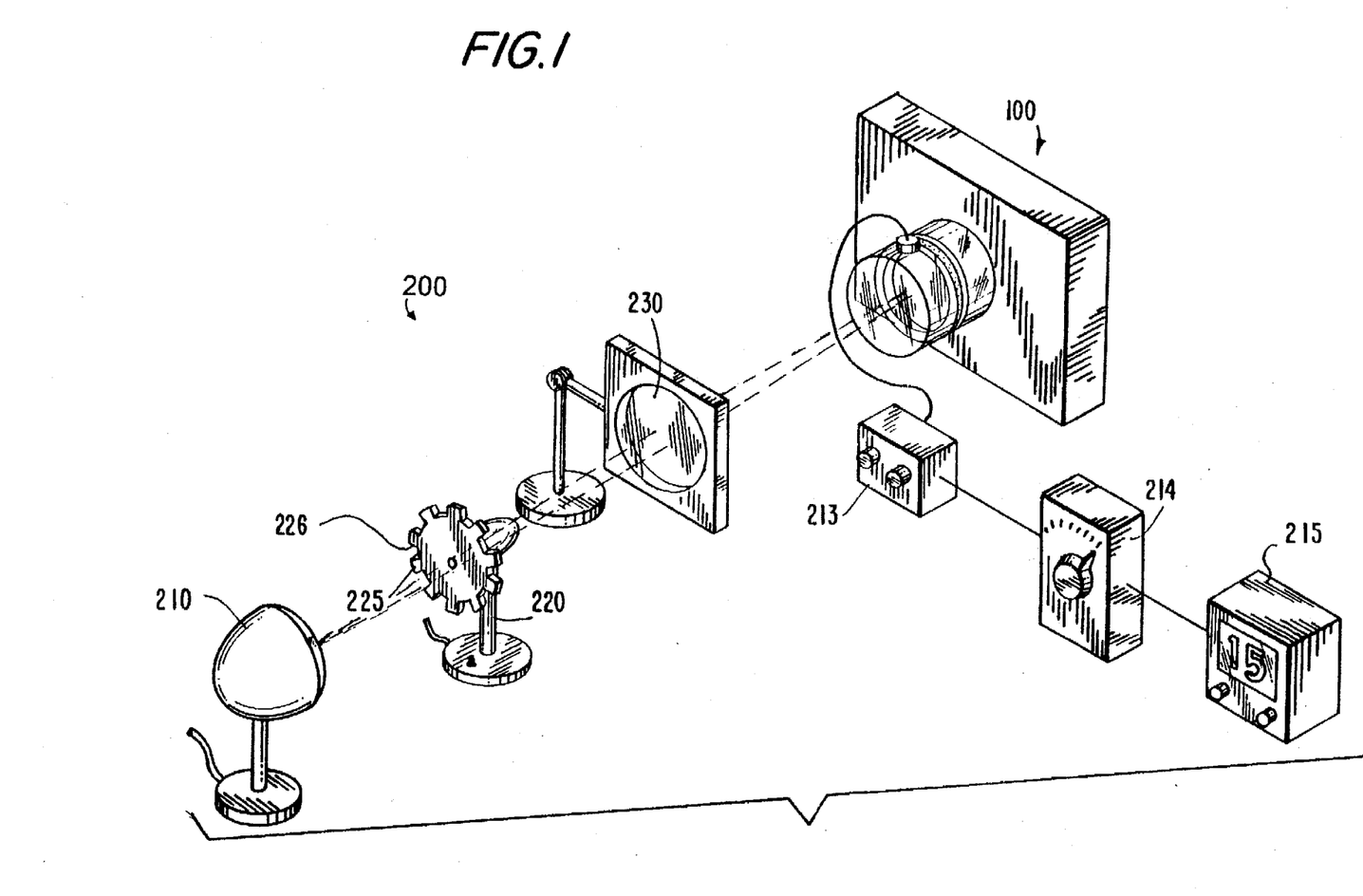
FIG. 1 is a schematic perspective view of an apparatus for measuring the thermal conductivity or resistivity of a thin film in accordance with an embodiment of the invention.

An apparatus for measuring the amplitude of sound generated by modulated illumination of a thin film is shown generally as thermal resistance detector 200 in FIG. 1. Apparatus 200 includes a light source 210 for illuminating a sample mounted in a measuring cell 100 with pulses of energy. Light source 210 can be a laser, a light emitting diode, an incandescent lamp such as a halogen bulb commonly used for an automobile headlight optionally coupled with an appropriate condenser or other appropriate sources of energy.

Apparatus 200 preferably also includes a mechanism for modulating the energy from source 210 onto a test sample. In one embodiment of the invention, the light emitted from light source 210 is modulated with a modulation device 220 in the form of a mechanical light chopper constructed with a rotating metal disk 225 having a plurality of notches 226 formed in the edge of the disk. Alternatively, holes, rather than notches can be used. By varying the rate at which disk 225 revolves, the light emitted from source 210 can be modulated at a selected frequency in a highly accurate manner. For example, if disk 225 includes 10 notches 226 and is spun at 1,200 rpm, the light will be modulated at a frequency of 200 Hz. There are many other suitable ways of modulating the light from source 210. For example, the light source can be strobed, a lens directing the beam or other means can be used to move the light beam on and off the sample, a mechanical shutter can be opened and closed, a liquid crystal light shutter can be opened and closed. Modulation of the beam can also be accomplished through an electro-optical or acousto-optical modulator, a laser scanner and various other known ways of modulating a beam of light can be employed.

After light leaves modulation device 220, it passes through a focusing lens 230. Alternatively, focusing lens 230 can be interposed between modulation device 220 and light source 210. In other embodiments, focusing lens 230 is not included. Steering the beam of light can also be accomplished with a mechanical mirror scanner, an acousto-optical deflector or other suitable means. Moreover, modulation device 220 can include a mechanism for using lens 230 to direct light on and off the sample at the desired frequency, rather than interrupting the beam. In alternative embodiments, such as if a laser or other arrangement is used as the light source, lens 230 and light modulation device 220 are unnecessary.

Measuring cell 100 is shown having a sample substrate 10 mounted thereon. A test portion 15 of the substrate of sample 10 is coated with a thin film 30. The entire surface of substrate 10, including both test portion 15 and a control portion 16 which does not support thin film 30 is coated with a covering film 40. Covering film 40 is preferably highly thermally conductive and opaque. Suitable materials include graphite and metals. A back surface 11 of substrate 10 is mounted in contact against a large heat sink 20 formed of a material with high thermal conductivity such as copper or aluminum. If the differential method is not to be used, substrate 10 would be covered with thin film 30 only.

A sound chamber 75 of test cell 100 is then assembled over substrate 10. In the embodiment shown in FIGS. 1–3, O-ring spacer 50 is disposed around the edge of the top surface of substrate 10 and a glass block cover 60 is disposed thereon. Glass cover 60 is transparent to the light to be used to illuminate the surface of covering film 40. Glass cover 60 also includes an acoustic duct 70, which faces sample 10 and is constructed to permit sound waves to travel to a microphone 80, disposed in a channel 85 within glass cover 60. Sound chamber 75 can be filled with air, or other gases such as helium which can produce pressure changes of greater magnitude, leading to enhanced sensitivity and signal to noise ratio. Channel 85 is coupled to duct 70 and acoustically sealed internal sound chamber 75 is thereby formed by glass cover 60, substrate 10 and O-ring 50. The size of chamber 75 and the distance from film 40 to microphone 80 is typically significantly less than the wavelength of the sound produced. Thus, microphone 80 generally measures pressure changes within chamber 75. Alternate constructions of test cell 100 are also suitable. In fact, with suitable equipment, an acoustic chamber is not necessary.

Figure 2:
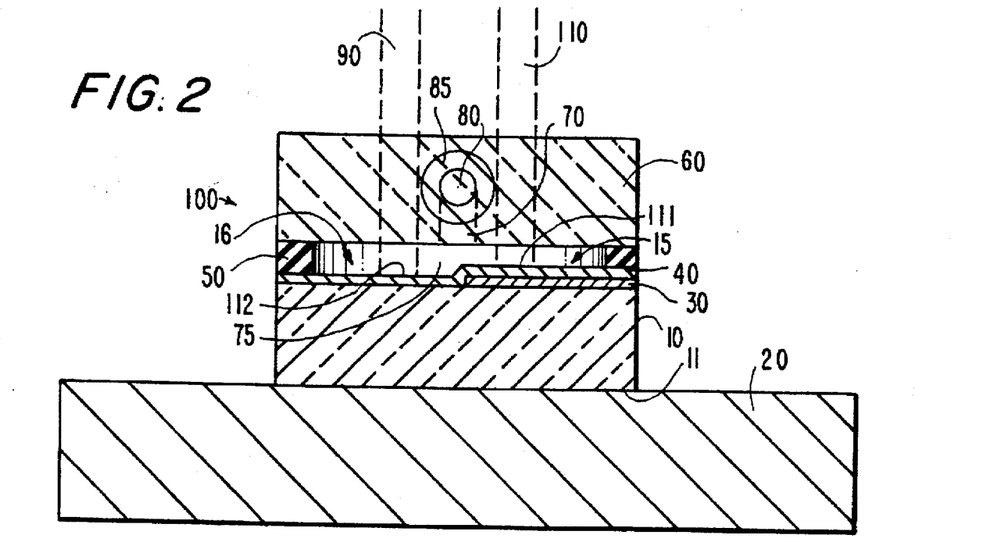
FIG. 2 is a schematic view of a measuring cell of the apparatus of FIG. 1, in accordance with an embodiment of the invention.

Referring to FIG. 2, a beam of light 110 is shown passing through glass cover 60 to strike the surface of covering film 40 at a test position 111 over thin film 30 on test portion 15 of substrate 10. When the differential method is used, after measurements are taken at test position 111 where cover film 40 overlaps thin film 30, the beam is directed onto cover film 40 at a control position 112 on control portion 16 of substrate 10 where cover film is not over thin film 30, but is directly on substrate 10. This beam is designated beam 90. Positions 111 and 112 are preferably equally distant from microphone 80 to reduce minor variations that can be caused by differences in distance. Switching between beams 90 and 110 can be accomplished by moving lens 230, with a dual shutter system and two lenses or any other appropriate method. By subtracting the amplitude of the sound created when illuminating control position 112 from test position 111, the remainder is attributable to the thermal resistance of thin film 30 ($R_f$) only and the other thermal resistance involved drop out of the calculation.

In an alternative embodiment, the differential registration method can be implemented by switching a light beam of constant intensity between test portion 15 and control portion 16 of substrate 10 at the same frequency as the light would be modulated in the differential method described above. When the size of the acoustic chamber is much smaller than the wavelength of the sound generated at the sample surface, such switching of the beam will produce modulation of the pressure in the chamber equal to the difference of the pressure amplitudes from the test and control portions of the sample. This modulation in pressure therefore generates a pure differential signal that can be detected by microphone 80 and electronically processed in the manner similar to the differential method described above. Because it is proportional to the thermal resistance of the tested thin film only, there is no need to substract results from the two sides.

Referring again to the embodiment shown in the figures, when beams 90 or 110 are used to illuminate cover film 40 in a modulated manner, an acoustical signal is generated. In the embodiment illustrated, the signal is received by microphone 80 which produces an electrical signal. The signal is amplified with a preamplifier 213 and then passes through a band pass filter 214. Band pass filter 214 is tuned to a frequency equal to the modulation or scanning frequency. The modulation frequency is advantageously in the range of 100–500 Hz for certain films and this depends on film thickness and material used as discussed below. It has been found that background noise tends to be well below the modulation or scanning frequency and therefore, acceptable results can be achieved by filtering frequencies below the modulation or scanning frequency with a high pass filter and ignoring background noise from signals above that frequency. Alternatively, a phase sensitive or "lock-in" detector can be used in place of a band pass filter, or in addition to it for increased signal to noise ratio and higher sensitivity. From filter 214, the signal proceeds to a data acquisition system 215, which can be in the form of a simple volt meter, a chart recorder, a computerized data processing system and the like.

The procedure for determining the magnitude of the thermal resistance of a thin film by measuring the amplitude of the acoustics signal generated by modulating light onto the surface of the film is based on the following physical principals.

The amplitude of the Fourier component of the sound produced in the gas near the surface of the film, due to the periodic surface temperature change ($\Delta T$) at the modulation frequency ($f_0$) is proportional to $\Delta T$ in the small signal approximation. This is true with the method described herein, because $\Delta T$ will not exceed a few °C. and the maximum modulation frequency can be limited to a few hundred Hertz as discussed below. Furthermore, the heat input rate (Q) is determined by the intensity of the light beam, which can be kept constant, and the reflectance of the thin film will be constant if the same type of sample is to be measured. Alternatively, the reflectance over the substrate can be kept constant if the differential method, discussed below, is used and a film such as a graphite or metal film is consistently used as cover film 40. Thus, the reflectance will not change from sample to sample.

Therefore, since amplitude is proportional to $\Delta T$, amplitude is proportional to thermal resistance ($A \propto R$). The temperature difference between the illuminated surface and the heat sink to which the sample is mounted is directly proportional to the total thermal resistance (R) from the film surface to the heat sink, i.e., the change in surface temperature is equal to the rate of heat input multiplied by the thermal resistance, assuming an established heat flow condition, as set forth below in formula II.

$$\Delta T = QR \quad \text{(II)}$$

The thermal resistance (R) is comprised of the thermal resistance of the optional covering film of graphite or metal ($R_g$) (optional), the effective resistance of the film to be measured ($R_f$), the resistance of the substrate ($R_s$) on which the thin film is disposed and, generally, the heat transfer resistance at the interface between the substrate and the heat sink ($R_i$). Thus, $R=R_g+R_f+R_s+R_i$. When the differential method is used, all of these components, except $R_f$ are negated, because $R_g$, $R_s$ and $R_i$ will be substantially the same for test side 15 and control side 16, provided that they do not significantly exceed $R_f$, so that the uncertainty in measurement of R is minimal, compared to $R_f$.

To estimate the possible magnitudes of $R_g$, $R_f$, $R_s$, and $R_i$, it should be noted that the metal films and graphite films that are optionally used as the top opaque coating intrinsically possess a high thermal conductivity (approximately 140 W/mK for bulk crystalline graphite). Therefore, even with the worst case assumption, if the thin film thermal conductivity ($k_g$) is ten times lower than in the bulk metal or graphite, the thermal resistance for graphite $R_g$ can be estimated as follows in formula III:

$$R_g = d_g/\{(\pi a^2/4)k_g\} \sim 0.085 \text{ K/W} \quad \text{(III)}$$

for a beam diameter of a=1 mm and a graphite film thickness $d_g$=1 μm.

Typical dielectric films, such as various metal oxide films used for optical coatings or silicon dioxide films used for microelectronic devices will have a much higher thermal resistance than that for an opaque graphite covering layer. The thermal conductivities $k_f$ of these materials are typically less than 1 W/mK. Assuming a film thickness of 1 μm, the thermal resistance of a silicon dioxide film can be calculated as follows in formula IV:

$$R_f > d_f/\{(\pi a^2/4)k_f\} \sim 1.3 \text{ K/W} \quad \text{(IV)}$$

The thermal resistance of a substrate with a diameter much larger than the diameter of the beam of light striking the surface of the substrate, a, is approximated by the following formula V:

$$R_s = 1/(2k_s a) \sim 3.3 \text{K/W} \quad \text{(V)}$$

assuming that silicon, having a conductivity $k_s$=150 W/mK, is used as the substrate material.

The final approximation is based on the large surface area of the substrate/heat sink interface $R_i$, which can be lowered to as little as 0.01 K/W with a substrate diameter of one inch, if thermal grease having a surface thermal resistance of 0.05 K/Wcm² is used between the substrate and heat sink. It should also be noted that the substrate itself can be used as the heat sink, as will be shown below, provided that it has a sufficient thermal capacity compared to the amount of heat generated during the measurement procedure.

From the above illustrative estimates, it can be seen that the thermal resistance of the thin film ($R_f$) measured typically constitutes a sufficiently significant portion of the overall thermal resistance of the sample (R) tested. Furthermore, when the differential method is used, all factors except the thermal resistance of the thin film drop out of the calculation for even higher accuracy.

In a preferred embodiment of the invention, the thermal conductivity of a thin film is measured by a differential method as follows. If differential registration is considered, between a dual layer side of a substrate having a cover film and a thin film layer and compared to a single layer side of the substrate having only a cover film, the above analysis can be simplified and the readings determined with greater accuracy and sensitivity. The difference in the amplitudes of acoustic signals from the two layer side and single layer control side is equal to the amplitude of the signal for the thin film itself and proportional to the thermal resistance of the thin film. When the "switching" differential method is used, only the difference is measured. This value can be easily converted into the effective thermal conductivity coefficient of the film, as long as the film's physical thickness is known.

The above measurements depend on an established heat flow during the modulation cycle. Thus, the frequency of modulation or of switching on and off the surface should not exceed the inverse heat dissipation rate at the surface of the sample. It is advantageous if the frequency of modulation ($f_0$) is selected so that the penetration depth of the temperature modulation of the thin film $l_f=(2\pi f_0/\Lambda_f)^{-1/2}$ as well as that of the substrate $l_s=(2\pi f_0/\Lambda_s)^{-1/2}$ are more than about 100 times the combined thickness of the thin film and substrate ($l_f$ and $l_s$ >100 ($d_f+d_s$)).

In an alternative method, the modulation frequency $f_0$ is set too high for the temperature modulation to penetrate through both the film(s) and substrate, and at the same time, low enough for the temperature modulation to penetrate the film or films. Under these conditions, the substrate will effectively perform as the heat sink and the thermal resistance of the interface of the substrate and the heat sink is eliminated from the calculation. Accordingly, the penetration depth of the temperature modulation in the film $l_f=(2\pi f_0/\Lambda_f)^{-1/2}$ should be much larger than the film thickness ($l_f>>d_f$), and the penetration depth of temperature modulation in the substrate ($l_s=(2\pi f_0/\Lambda_s)^{-1/2}$) should be much shorter than the substrate thickness ($l_s<<d_s$) (wherein $\Lambda_f$ and $\Lambda_s$ are the thermal diffusivity of the film and substrate, respectively). In this embodiment, the modulation frequency ($f_0$) is advantageously selected so that the thin film temperature modulation penetration depth $l_f$ is at least about 100 times larger than the thin film thickness and the substrate temperature modulation penetration depth $l_s$ is about 100 times less than the substrate thickness.

As an example of this embodiment, in the case of a silicon substrate disk 6 mm thick, with a thermal diffusivity of 0.915 cm²/sec, and a film 1 μm thick with an estimated thermal diffusivity of 6×10⁻³ cm²/sec, which is typical for $SiO_2$, the modulation frequency $f_0$ should be in the range:
0.4 Hz<<$f_0$<<90 kHz Under these conditions, the amplitude of the temperature modulation is established with the following formula VI:

$$\Delta T \cong Q_0/[k_s(2\pi f_0/\Lambda_s)^{1/2}]+Q_0 R_f \quad \text{(VI)}$$

wherein:
 $Q_0$ is the amplitude of the heat flux modulation;
 $k_s$ is the thermal conductivity of the substrate;
 $f_0$ is the modulation frequency;
 $\Lambda_s$ is the thermal diffusivity of the substrate; and
 $R_f$ is the thermal resistance of the thin film.

The second term in this equation ($Q_0 R_f$) is what is measured in the differential method and it is proportional to the thermal resistance of the film $R_f$.

For the most accurate measurements, the film should be deposited onto a substrate with a thermal conductivity ($k_s$) that is much higher than the effective thermal conductivity of the film ($k_f$) in order to minimize the first term in equation (VI). Examples of advantageous substrate materials include silicon, diamond, copper, sapphire and so forth.

In order to prevent an undesirable temperature rise of the substrate during measurement, the sampling time should be short enough with respect to a given heat input and the thermal capacity of the sample to avoid raising the temperature of the sample more than a few degrees. For example, if the heat input is 0.3 W and the substrate is a 1 inch diameter×0.25 inch thick silicon disk, a sampling time of 3 seconds results in an average temperature rise of substantially less than 1° K. Sampling time of 1 to 10 seconds are advantageous under most circumstances and thin films in the range of 0.01 µm or even less to 1 µm and up to 5 µm and higher and can be measured with high sensitivity.

As is evident from the above, the thermal resistance and thermal conductivity are obtained in relative, device specific units. However, absolute calibration of the device can be accomplished readily by measuring the thermal conductivity of reference films of known thicknesses and known conductivities. Furthermore, the various parts of apparatus 200 can be assembled together in a single unit within a single housing in which coated samples are simply installed on a fixed heat sink; the modulation frequency can be controlled by turning a dial and the like, which can also simultaneously set the band filter; and the conductivity can be displayed in actual units of conductivity as opposed to volts. Because the voltage leaving the band filter is inversely proportional to conductivity, it is a simple matter to have the device convert volts into conductivity or resistivity with readily available technology. Collection of the data from the modulated beam procedure as well as manipulating the beam, calculating the differential of the signals from the test and control portion of the sample and conversion of data into thermal conductivity or resistance units can be done automatically by using an appropriate computer or microprocessor based controller.

The sensitivity of the method and apparatus described herein is sufficient for measuring the thermal conductivity of films with a thermal resistance as low as $1 \times 10^{-7}$ m²K/W. For example, if thermal conductivity $k_f$ is on the order of 0.1 W/mK (which is the case for a variety of optical coatings and thin films and in microelectronics) the conductivity of films as a thin as 0.01 µm can be measured.

In order to employ the differential method, an opaque film of metal, carbon or a graphite film having a thickness of a few micrometers can be deposited onto the surface of the sample by a number of various methods, including, but not limited to, spraying, vacuum evaporation, chemical vapor deposition, etc. However, it is important that the film is uniform. For example, in the spray method, a liquid consisting of small (less than 1 µm in diameter) graphite particles in a colloidal suspension in an appropriate volatile solute, such as isopropanol or acetone, is sprayed onto the surface of the sample as the sample rotates in planetary motion in its surface plane in order to obtain a spacially uniform coating. A suitable suspension can be formed by diluting Aerodag G, a colloidal suspension of graphite sold by Acheson of Port Huron, Mich., to a ratio of 10:1. The concentration of the suspension, the exposure time and as many other parameters as possible should be kept constant from sample to sample (including the reference sample) in order to promote high reproducibility of results. The spray method does not require vacuum conditions, is fast and non-invasive. The graphite film deposited can be easily wiped off with an appropriate solvent, such as isopropanol or acetone.

The following example is presented to illustrate a preferred embodiment of the invention. However, it should not be construed to limit the scope of the invention.

EXAMPLE 1

Silicon dioxide (SiO₂) coatings of different thicknesses were deposited onto the surface of disk shaped silicon substrates, each having a diameter of 1 inch and a thickness of 0.25 inches by two different methods. The first method was vacuum e-beam evaporation and the second method was thermal oxidation in a dry oxygen atmosphere at 1100° C. Half of the surface of each sample was etched with hydrofluoric acid to remove the SiO₂ film. The surface of each sample was then coated with a graphite film having a thickness of approximately 2 µm by the spray coat method under identical conditions. The average size of the colloidal graphite particles was 1 µm and the spray was driven by nitrogen gas at a pressure of 15 psi.

Samples were mounted in contact with a massive aluminum heat sink in the form of an aluminum disk having a diameter of about 4" and a thickness of about 1". A cover block of Pyrex® glass with an attached electret condenser microphone (Panasonic Model #WM-52BM) connected to a preamplifier, similar to the arrangement shown in FIGS. 1 to 3 was used. The light source was a 100 W halogen incandescent lamp coupled to a two-lens condenser with a focal length of approximately 100 mm. The beam was modulated at a frequency of 200 Hz with a mechanical chopper. The amplitude of the sound was detected by the microphone and the signal was amplified with the preamplifier.

Figure 3:
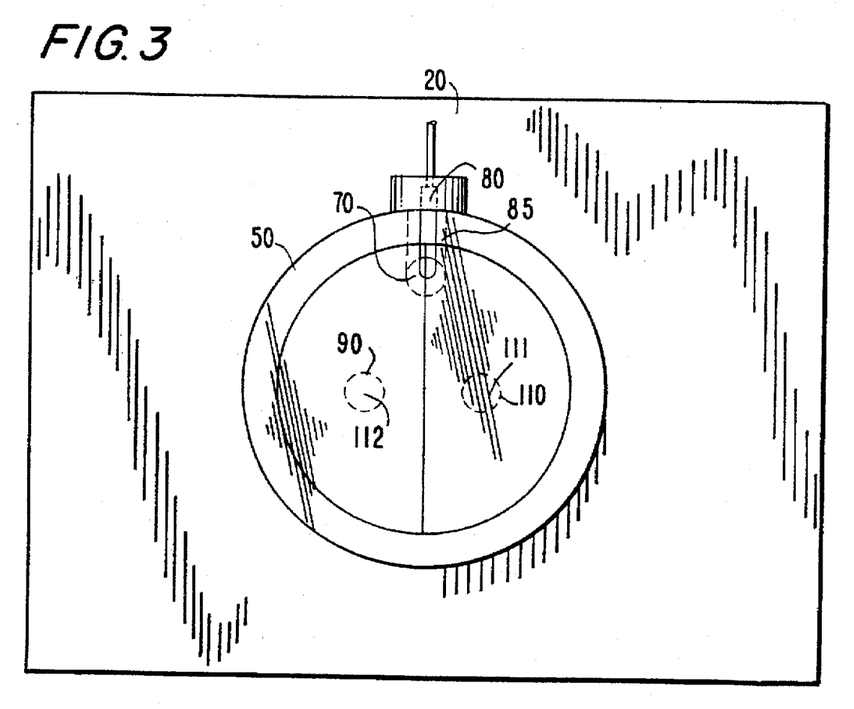
FIG. 3 is the top view of the measuring cell of FIG. 2.

The electrical signal from the preamplifier was high-pass filtered at approximately 200 Hz and measured with a conventional AC volt meter. For each sample, measurements were made alternatively from the test side and control side as shown in FIGS. 2 and 3, and at several locations at different distances from the acoustic duct. The signal amplitude differences were calculated at each pair of locations and then averaged over the surface of the sample. The sampling time for each measurement was approximately 2 seconds.

The apparatus was calibrated with a reference sample comprising a silicon substrate with a 56 µm thick plate of X-cut crystalline quartz optically contacted to the substrate surface. The thermal conductivity of the quartz plate was known because it was cut from a single crystal, not a grown thin film, and the thermal resistance at the interface between the quartz and the substrate was considered to be negligible, compared to the thermal resistance of the quartz plate itself, because the surfaces were optically contacted.

The device reading in volts obtained with the reference sample, was used to establish correspondence between device units (Volts) and units of thermal resistance. Since thermal resistance of the quartz plate was $9.876 \times 10^{-6}$ m²K/W and device reading was 1.56 V, the value of a device unit is $6.33 \times 10^{-6}$ m²K/W per 1 Volt.

Figure 4:
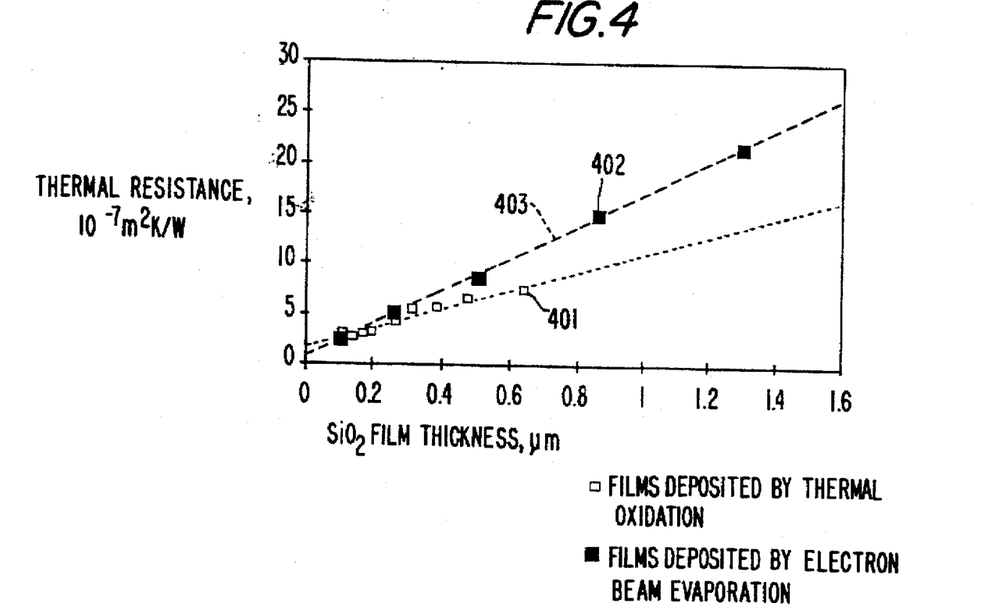
FIG. 4 is a graph showing the change in thermal resistance with film thickness of silicon dioxide films deposited onto monocrystalline silicon substrates using both electron beam vacuum evaporation and thermal oxidation of silicon in a dry oxygen atmosphere.
Figure 5:
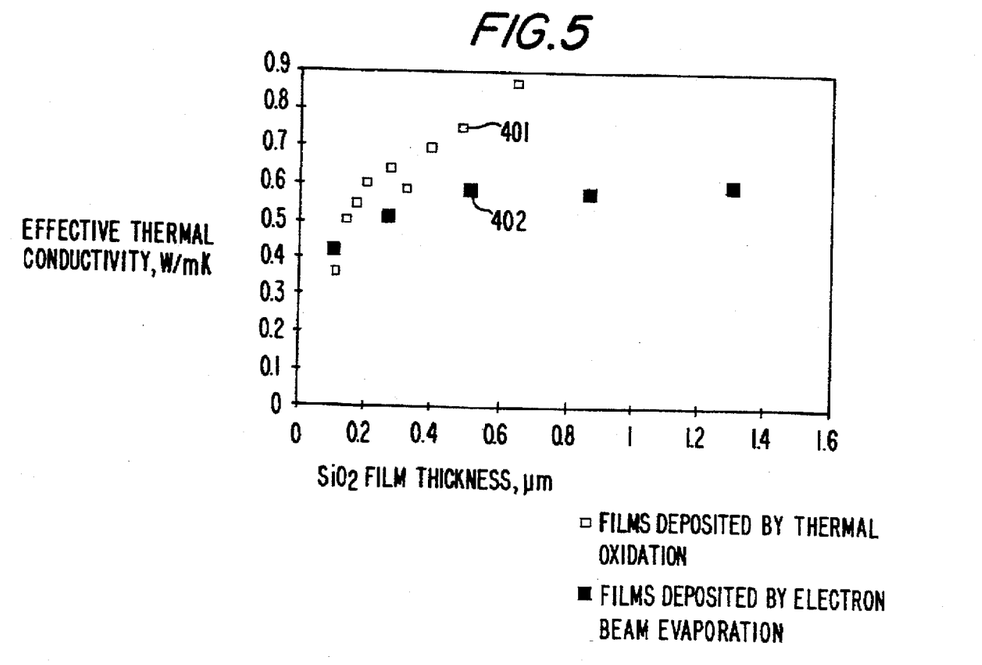
FIG. 5 is a graph showing the change in thermal conductivity with film thickness of silicon dioxide films deposited onto monocrystalline silicon substrates using both electron beam vacuum evaporation and thermal oxidation of silicon in a dry oxygen atmosphere.

A plot of thermal resistance versus thickness of the SiO₂ films is shown in FIG. 4 and the effective thermal conductivities of the films, versus film thicknesses, are plotted in FIG. 5. Open squares 401 correspond to measurements taken from the films deposited by thermal oxidation and filled in squares 402 correspond to measurements taken from films deposited by electron beam evaporation. The film thickness was determined by an optical reflectance method. The plot of thermal conductivity includes the contribution of the film/substrate interface thermal resistance and, is therefore the effective thermal conductivity.

As shown in FIG. 4, the thermal resistance of both the vacuum evaporated and thermally grown SiO₂ films demonstrate nearly linear increase in thermal resistance with thickness, as predicted. The deduced thermal conductivity coefficients are below the bulk thermal conductivity of amorphous SiO₂, which is reported to be in the range of 1.1–1.4 W/mK. However, as can be seen, the thermally grown oxide films exhibited considerably higher conductivities than the films formed by evaporation.

The thermal conductivities of the films themselves can be separated from the contribution of the film/substrate interface by estimating the slope of the linear fit to the plot of thermal resistance versus thickness data points. However, this is only valid to the extent the thin film thermal conductivity does not change with thickness. Such an approximation, shown by curve 403, yields a thin film thermal conductivity of 1.065 W/mK, and an interface resistance of $1.75 \times 10^{-7}$ m²K/W for the thermally grown films and a conductivity of 0.68 W/mK and an interface resistance of 0.77 m²K/W for the evaporated films. The results obtained are consistent with the findings of others, using different, more complicated measurement techniques involving the use of metal microstrips.

As demonstrated by the foregoing, it is possible to accurately measure the thermal conductivity of a thin film by measuring the acoustic signal generated when the thin film is heated with a pulse of energy, such as by shining modulated light on the film and then measuring the amplitude of the acoustic signal generated by the expansion of gas at the heated surface, every time the surface temperature is raised from the pulse of energy. By employing a differential method, in which a second layer of material is deposited on both a bare substrate as well as over the thin film to be measured, the results for that second layer can be subtracted to yield the portion of the signal generated by the thin film alone.

It will thus be seen that the objects set forth above, among those made apparent from the preceding description, are efficiently attained and, since certain changes may be made in carrying out the above methods and in the constructions set forth without departing from the spirit and scope of the invention, it is intended that all matter contained in the above description and shown in the accompanying drawings shall be interpreted as illustrative and not in a limiting sense.

It is also understood that the following claims are intended to cover all of the generic and specific features of the invention herein described, and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A method of obtaining data about the thermal resistance of a thin film of a first material on a substrate, comprising:

heating a thin film of a first material on a substrate with a pulse of energy of effective power to cause the thin film to increase in temperature and cause gas near the film to expand due to the increase in temperature of the heated thin film; and measuring the magnitude of the expansion.

2. The method of claim 1, wherein the thin film is heated with at least one pulse of electromagnetic radiation.

3. The method of claim 2, wherein the radiation is visible light and the intensity of the light onto the thin film is modulated at a selected frequency.

4. The method of claim 3, wherein the modulation frequency is selected so that the temperature modulation penetration depth of the thin film ($l_f$), represented by the formula $l_f = (2\pi f_0/\Lambda_f)^{-\frac{1}{2}}$ is at least about 100 times greater than the thin film thickness and the temperature modulation penetration depth of the substrate ($l_s$), represented by the formula $l_s = (2\pi f_0/\Lambda_s)^{-\frac{1}{2}}$ is less than about 1/100 of the substrate thickness, wherein $f_0$ is the modulation frequency, $\Lambda_f$ is the thermal diffusivity of the thin film and $\Lambda_s$ is the thermal diffusivity of the substrate.

5. The method of claim 3, wherein the modulation frequency is selected so that the temperature modulation penetration depth of the thin film ($l_s$) and the temperature modulation penetration depth of the substrate ($l_f$) are more than 100 times the combined thickness of the substrate and thin film, wherein $l_f = (2\pi f_0/\Lambda_f)^{-\frac{1}{2}}$, $l_s = (2\pi f_0/\Lambda_s)^{-\frac{1}{2}}$, $f_0$ is modulation frequency, $\Lambda_f$ is the thermal diffusivity of the thin film and $\Lambda_s$ is the thermal diffusivity of the substrate.

6. The method of claim 3, wherein the magnitude of the expansion is measured with a microphone which generates an electrical signal proportional to the magnitude of the expansion and at the selected frequency of modulation.

7. The method of claim 6, including the step of amplifying the electrical signal.

8. The method of claim 6, including the step of amplifying the electrical signal and filtering from the signal, at least frequencies below approximately the frequency of modulation.

9. The method of claim 8, including the step of converting the measured value of the signal to at least one of the thermal resistance or the thermal conductance of the thin film.

10. The method of claim 9, including comparing the amplitude of the amplified signal to preexisting values which correspond signal amplitudes to thermal resistances or conductances.

11. The method of claim 9, wherein the thin film has a thickness of from 0.01 to 5 μm and the thermal resistance or thermal conductance is accurate to 5%.

12. The method of claim 9, wherein the thin film has a thickness of from 0.01 to 1 μm and the thermal resistance or thermal conductance is accurate to 5%.

13. The method of claim 3, including providing a layer of a second material over the substrate at a test position where the first material is between the second material and the substrate and also at a control position where the first material is not between the second material and the substrate and directing the electromagnetic radiation at both the test position and the control position and measuring the magnitude of the expansion at both the test side and the control side.

14. The method of claim 13, including the step of subtracting the magnitude of the expansion at the control position from the magnitude of the expansion of the test position.

15. The method of claim 13, including the step of switching the light between the test position and the control position at the modulation frequency.

16. The method of claim 6, including providing a layer of a second material over the substrate at a test position where the first material is between the second material and the substrate and also at a control position where the first material is not between the second material and the substrate and directing the electromagnetic radiation at both the test position and the control position and measuring the magnitude of the expansion at both the test position and the control position.

17. The method of claim 16, wherein the second material is graphite.

18. A method of measuring the thermal resistance of a thin film of a first material, comprising:

forming a thin film of a first material over a portion of a substrate;

forming a layer of a second material over at least a portion of the first material at a test position and over a portion of a substrate not supporting the first material at a control position;

directing a beam of light that is modulated at a selected frequency onto the test position and measuring the amplitude of the sound waves generated as the gas adjacent the test position expands at the selected frequency as a result of modulated warming of the first and second materials from the modulated light;

directing a beam of light that is modulated at a selected frequency onto the control position and measuring the amplitude of the sound waves generated as the gas adjacent the control position expands at the selected frequency as a result of modulated warming of the second material from the modulated light; and subtracting the amplitude of the sound signal from the test portion from the sound signal at the control position.

19. The method of claim 18, wherein the light is modulated onto the surface of the control position at a frequency selected so that the temperature modulation penetration depth of the first and second ($l_f$), represented by the formula $l_f=(2\pi f_0/\Lambda_f)^{-\frac{1}{2}}$ is at least about 100 times greater than the thickness of the first and second materials and the temperature modulation penetration depth of the substrate ($l_s$), represented by the formula $l_s=(2\pi f_0/\Lambda_s)^{-\frac{1}{2}}$ is less than about 1/100 of the substrate thickness, wherein $f_0$ is the modulation frequency, $\Lambda_f$ is the thermal diffusivity of the first and second material and $\Lambda_s$ is the thermal diffusivity of the substrate.

20. The method of claim 17, wherein the frequency is selected so that the temperature modulation penetration depth of the first and second material ($l_f$) and the temperature modulation penetration depth of the substrate ($l_s$) are more than 100 times the combined thickness of the substrate and first and second materials, wherein $l_f=(2\pi f_0/\Lambda_f)^{-\frac{1}{2}}$, $l_s=(2\pi f_0/\Lambda_s)^{-\frac{1}{2}}$, $f_0$ is modulation frequency, $\Lambda_f$ is the thermal diffusivity of the first and second materials and $\Lambda_s$ is the thermal diffusivity of the substrate.

21. The method of claim 18, wherein the second material is graphite.

22. The method of claim 20, wherein the substrate supporting the thin film is silicon.

23. The method of claim 18, including the step of contacting the substrate supporting the thin film to a heat sink.

24. The method of claim 17, wherein the light is modulated by directing it back and forth between the control position and the test position at the modulation frequency.

25. A method of measuring the thermal resistance of a thin film of a first material, comprising:

forming a thin film of a first material over a test position of a substrate;

forming a layer of a cover material over the first material at the test position and over a portion of the substrate not supporting the first material at a control position;

directing a beam of light back and forth between the test position and the control position at a selected frequency, the beam of light of sufficient power to raise the surface temperature at both the test and control position; and measuring the modulated pressure differential caused by the different warming of the test and control positions caused by the difference in thermal resistance.

26. An apparatus for obtaining data about the thermal resistance of a thin film on a substrate, comprising:

a holder for mounting a substrate having a thin film of material disposed thereover;

a source for a pulse of energy for heating the thin film sufficiently to expand gas adjacent the thin film; and sound detection means for measuring the magnitude of the gas expansion as a result of the heating from the pulse of energy.

27. The apparatus of claim 26, wherein the source of energy is a source of electromagnetic radiation modulated at a selected frequency.

28. The apparatus of claim 27, wherein the sound detection means includes a microphone which generates an electrical signal upon detecting a sound wave caused by the gas expanding, the signal at the frequency of modulation and proportional to the amplitude of the sound wave.

29. The apparatus of claim 27, wherein the sound detection means includes a microphone which generates an electrical signal upon detecting a sound wave caused by the gas expanding and a filter and an amplifier for filtering and amplifying the electrical signal.

30. The apparatus of claim 28, including a display for displaying a value proportional to the strength of the electrical signal.

31. The apparatus of claim 30, wherein the display includes a volt meter.

32. The apparatus of claim 26, wherein the apparatus includes a thin film with a thickness of 0.01 to 5 μm on a substrate.

33. The apparatus of claim 26, wherein the apparatus includes a thickness of 0.01 to 1 μm.

34. The apparatus of claim 29, including at least one light modulation device that modulates light onto the thin film, selected from the group consisting of light choppers, electro-optical devices and acousto-optical devices which can be operated at a selected frequency to modulate the light at the selected frequency.

35. The apparatus of claim 26, wherein the source of pulsed energy is selected from the group consisting of LED's and lasers.

36. The apparatus of claim 26, wherein the source of pulsed energy is an incandescent bulb.

37. The apparatus of claim 29, including a chamber at the surface of the thin film and the chamber is filled with air.

38. The apparatus of claim 29, including a chamber at the surface of the thin film and the chamber is filled with helium.

39. The apparatus of claim 28, including a chamber transparent to the electromagnetic radiation positioned to be over the thin film so that the gas expands within the chamber.

* * * * *